United States Patent
St. Goar et al.

[19]

[11] Patent Number: 5,807,318
[45] Date of Patent: Sep. 15, 1998

[54] METHOD OF PERFUSING THE CORONARY VASCULATURE

[75] Inventors: Frederick G. St. Goar, Menlo Park, Calif.; William S. Peters, Victoria, Australia; Philip C. Evard; Stephen W. Boyd, both of Palo Alto, Calif.; Craig L. Adams, San Ramon, Calif.; Richard L. Mueller, Jr., Byron, Calif.; John H. Stevens, London, England

[73] Assignee: Heartport, Inc., Redwood City, Calif.

[21] Appl. No.: 615,152

[22] Filed: Mar. 12, 1996

Related U.S. Application Data

[60] Division of Ser. No. 351,850, Dec. 7, 1994, which is a continuation-in-part of Ser. No. 282,192, Jul. 28, 1994, Pat. No. 5,584,803.

[51] Int. Cl.$^6$ .................................................. A61M 1/00
[52] U.S. Cl. ............................................................ 604/53
[58] Field of Search ................................... 604/96, 101, 4, 604/52, 53, 264, 280, 113, 51; 606/194, 192; 128/772; 600/18

[56] References Cited

U.S. PATENT DOCUMENTS

| | | |
|---|---|---|
| 3,788,328 | 1/1974 | Alley et al. . |
| 3,903,895 | 9/1975 | Alley et al. . |
| 4,248,224 | 2/1981 | Jones . |
| 4,285,341 | 8/1981 | Pollack . |
| 4,287,892 | 9/1981 | Schiff . |
| 4,327,709 | 5/1982 | Hanson et al. . |
| 4,540,399 | 9/1985 | Litzie et al. . |
| 4,610,661 | 9/1986 | Possis et al. . |
| 4,658,817 | 4/1987 | Hardy . |
| 4,712,551 | 12/1987 | Rayhanabad . |
| 4,714,460 | 12/1987 | Calderon . |

(List continued on next page.)

FOREIGN PATENT DOCUMENTS

WO 91/08791   6/1991   WIPO .

OTHER PUBLICATIONS

Uchida et al., "Percutaneous Fiberoptic Angioscopy of the Cardiac Valves," *American Heart Journal*, 1991;121(6, PartI):1791–1798.

Yamaguchi et al. "A Case of a Reoperation Using a Balloon Catheter with Blocked Pars Ascendes Aortae" *Kyobu Geka*, 42(11):961–964 (1989).

"Cartoid Artery Shunts—A complete line of balloon occlusive, tapered, and straight models." Research Medical, Inc. (2 pages).

(List continued on next page.)

*Primary Examiner*—Manuel Mendez
*Attorney, Agent, or Firm*—Jeffry J. Grainger; Jens E. Hoekendijk

[57] ABSTRACT

A catheter system is provided for accessing the coronary ostia transluminally from a peripheral arterial access site, such as the femoral artery, and for inducing cardioplegic arrest by direct infusion of cardioplegic solution into the coronary arteries. In a first embodiment, the catheter system is in the form of a single perfusion catheter with multiple distal branches for engaging the coronary ostia. In a second embodiment, multiple perfusion catheters are delivered to the coronary ostia through a single arterial cannula. In a third embodiment, multiple perfusion catheters are delivered to the coronary ostia through a single guiding catheter. In a fourth embodiment, multiple catheters are delivered to the coronary ostia through a single guiding catheter which has distal exit ports that are arranged to direct the perfusion catheters into the coronary ostia. In each embodiment, the catheters are equipped with an occlusion means at the distal end of the catheter for closing the coronary ostia and isolating the coronary arteries from the systemic blood flow. The occlusion means can take the form of an inflatable occlusion balloon cuff, a tapered occlusion device or an O-ring encircling the distal end of the catheter. An optional ventricular venting catheter can be included in the system for venting blood and fluids from the left ventricle of the heart. The catheter system is combined with a femoral-to-femoral cardiopulmonary bypass system to provide a system for cardioplegic arrest and total cardiopulmonary support during minimally invasive cardiac surgical procedures.

20 Claims, 11 Drawing Sheets

U.S. PATENT DOCUMENTS

| | | |
|---|---|---|
| 4,770,652 | 9/1988 | Mahurkar . |
| 4,771,777 | 9/1988 | Horzewski et al. . |
| 4,790,825 | 12/1988 | Bernstein et al. . |
| 4,804,358 | 2/1989 | Karcher et al. . |
| 4,804,359 | 2/1989 | Grunwald et al. . |
| 4,804,365 | 2/1989 | Litzie et al. . |
| 4,820,271 | 4/1989 | Deutsch . |
| 4,832,028 | 5/1989 | Patel . |
| 4,877,035 | 10/1989 | Bogen et al. . |
| 5,000,743 | 3/1991 | Patel et al. . |
| 5,009,636 | 4/1991 | Wortley et al. . |
| 5,011,469 | 4/1991 | Buckberg et al. . |
| 5,021,045 | 6/1991 | Buckberg et al. ............... 604/96 |
| 5,041,098 | 8/1991 | Loiterman et al. . |
| 5,106,368 | 4/1992 | Uldall et al. . |
| 5,122,115 | 6/1992 | Marks . |
| 5,122,125 | 6/1992 | Deuss . |
| 5,125,924 | 6/1992 | Rudko . |
| 5,125,926 | 6/1992 | Rudko et al. . |
| 5,171,232 | 12/1992 | Castillo et al. . |
| 5,195,942 | 3/1993 | Weil et al. . |
| 5,222,941 | 6/1993 | Don Michael . |
| 5,312,344 | 5/1994 | Grinfeld et al. . |
| 5,324,260 | 6/1994 | O'Neill et al. . |
| 5,370,640 | 12/1994 | Kolff . |
| 5,374,245 | 12/1994 | Mahurkar . |
| 5,411,027 | 5/1995 | Wiklund et al. . |
| 5,433,700 | 7/1995 | Peters ............... 604/4 |
| 5,451,207 | 9/1995 | Yock . |
| 5,458,574 | 10/1995 | Machold et al. ............... 604/101 |
| 5,476,453 | 12/1995 | Mehta . |
| 5,478,309 | 12/1995 | Sweezer et al. . |
| 5,487,730 | 1/1996 | Marcadis et al. . |
| 5,525,388 | 6/1996 | Wand et al. . |
| 5,527,292 | 6/1996 | Adams et al. . |
| 5,558,644 | 9/1996 | Boyd et al. ............... 604/96 |
| 5,584,803 | 12/1996 | Stevens et al. ............... 604/4 |

OTHER PUBLICATIONS

Menasche, p. "Experimental Comparison of Manually Inflatable Versus Autoinflatable Retrograde Cardioplegia Catheters," Ann Thorac Surg, 58:533–5 (1994).

Menasche et al. "Retrograde Coronary Sinus Perfusion: A Safe Alternative for Ensuring Cardioplegic Delivery in Aortic Valve Surgery," Ann Thorac Surg, 34(6):647–658 (1982).

Reed et al. "Cardiopulmonary Perfusion" Texas Medical Press, Inc., Houston, Texas, 1975.

William Harvey, Left Ventricular Vent Cannulae Type 1891/Type 1892/Type 1895, BARD Cardiopulmonary Division, p. B57.

William Harvey, Molina Coronary Perfusion Cannulae Type 1880 and Type 1881, BARD Cardiopulmonary Division, p. B53.

William Harvey, DeBakey Coronary Perfusion Cannulae Type 1870, BARD Cardiopulmonary Division, p. B31.

Accessories de Perfusion Coronaire, New Cardicorp S.A., Rue Saint–Pierre 6, 1701 Fribourg, Switzerland.

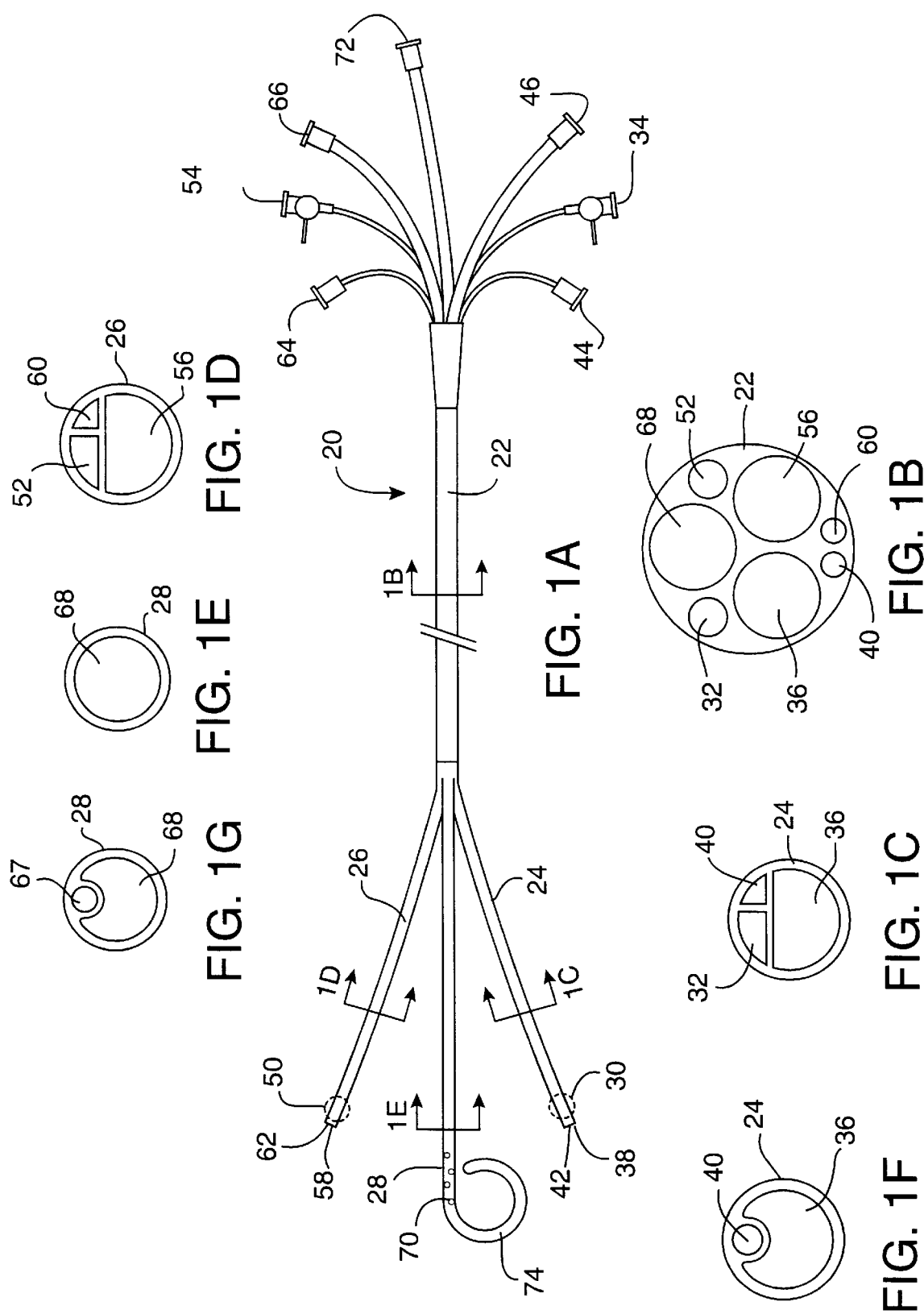

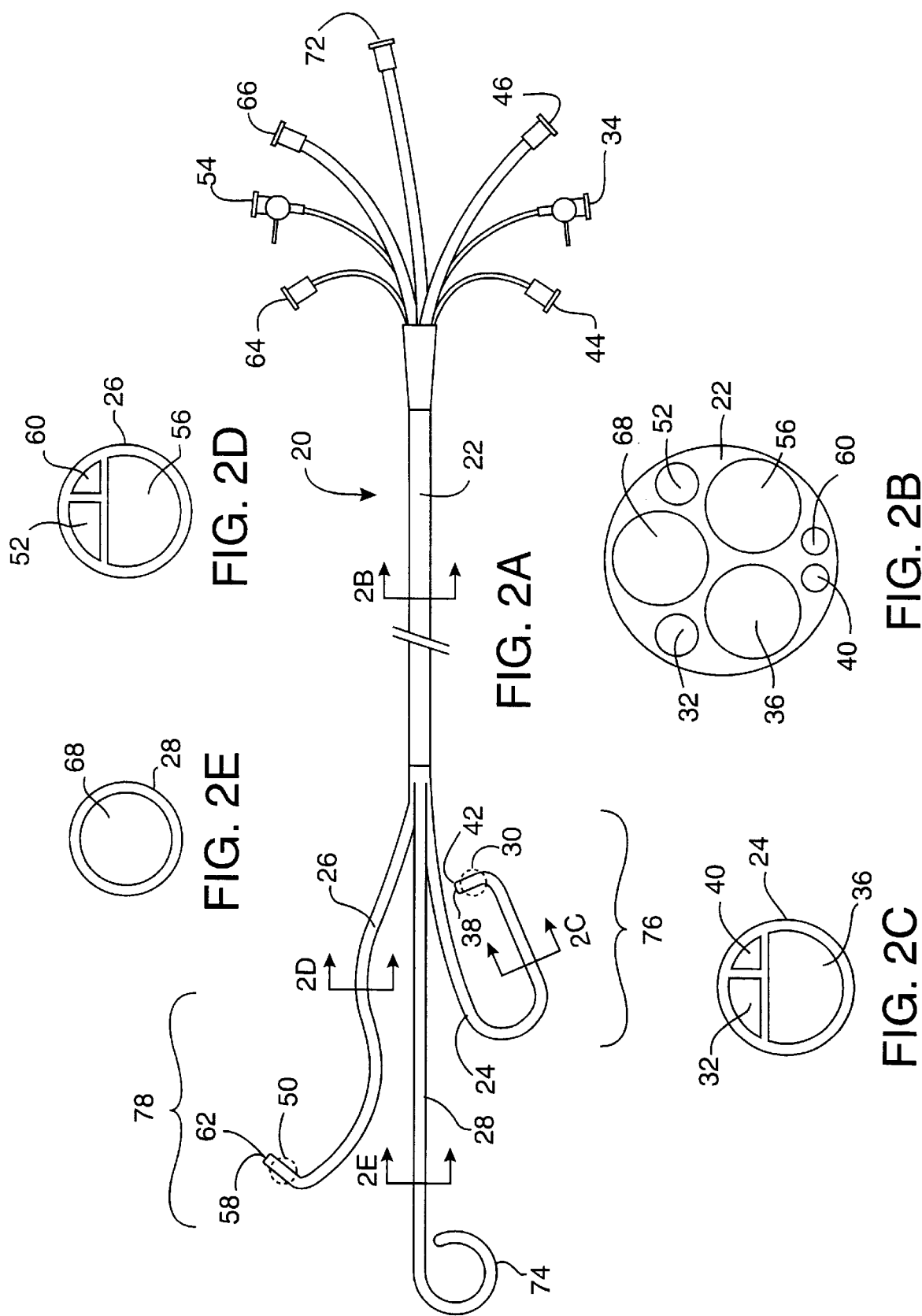

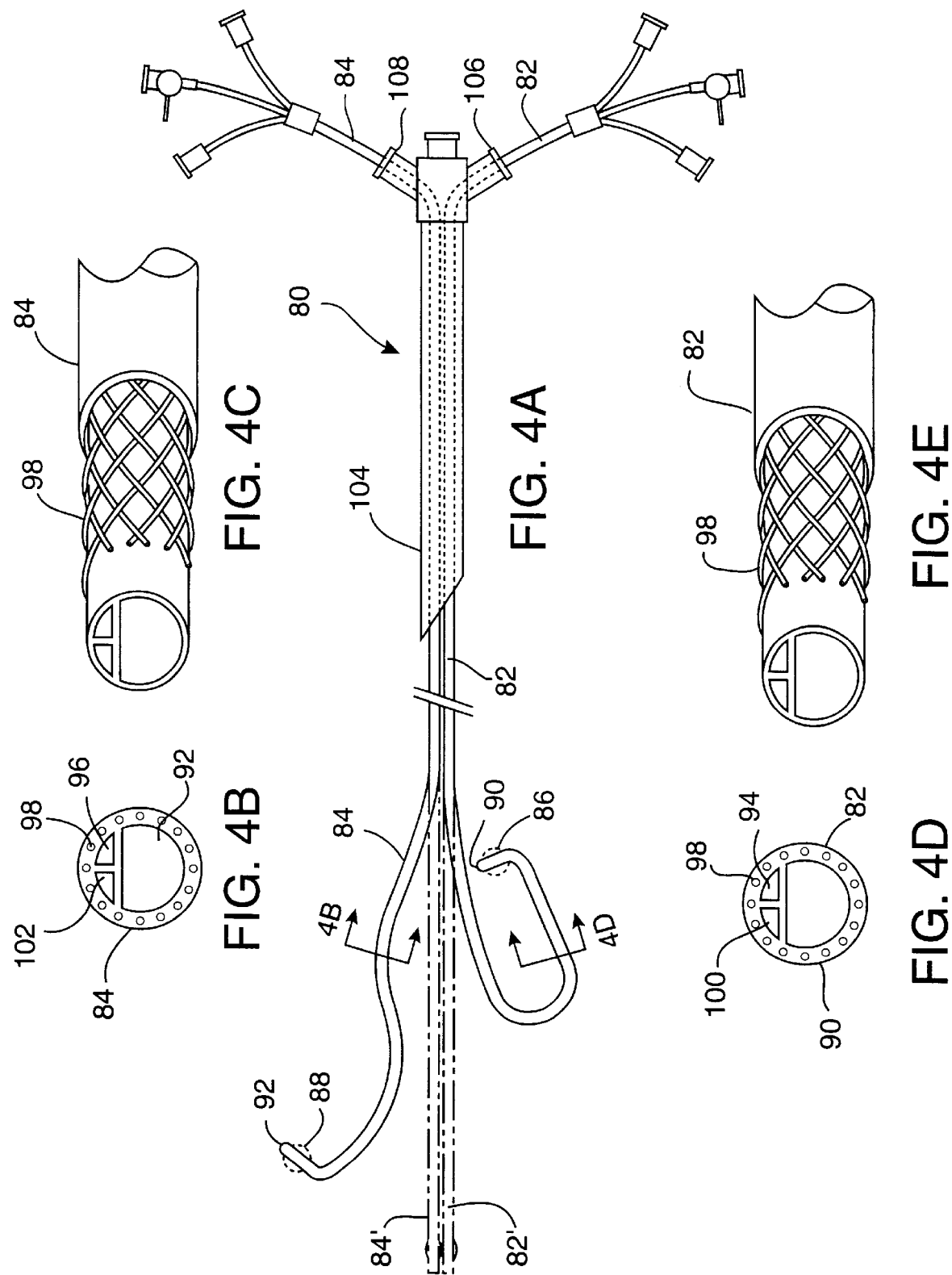

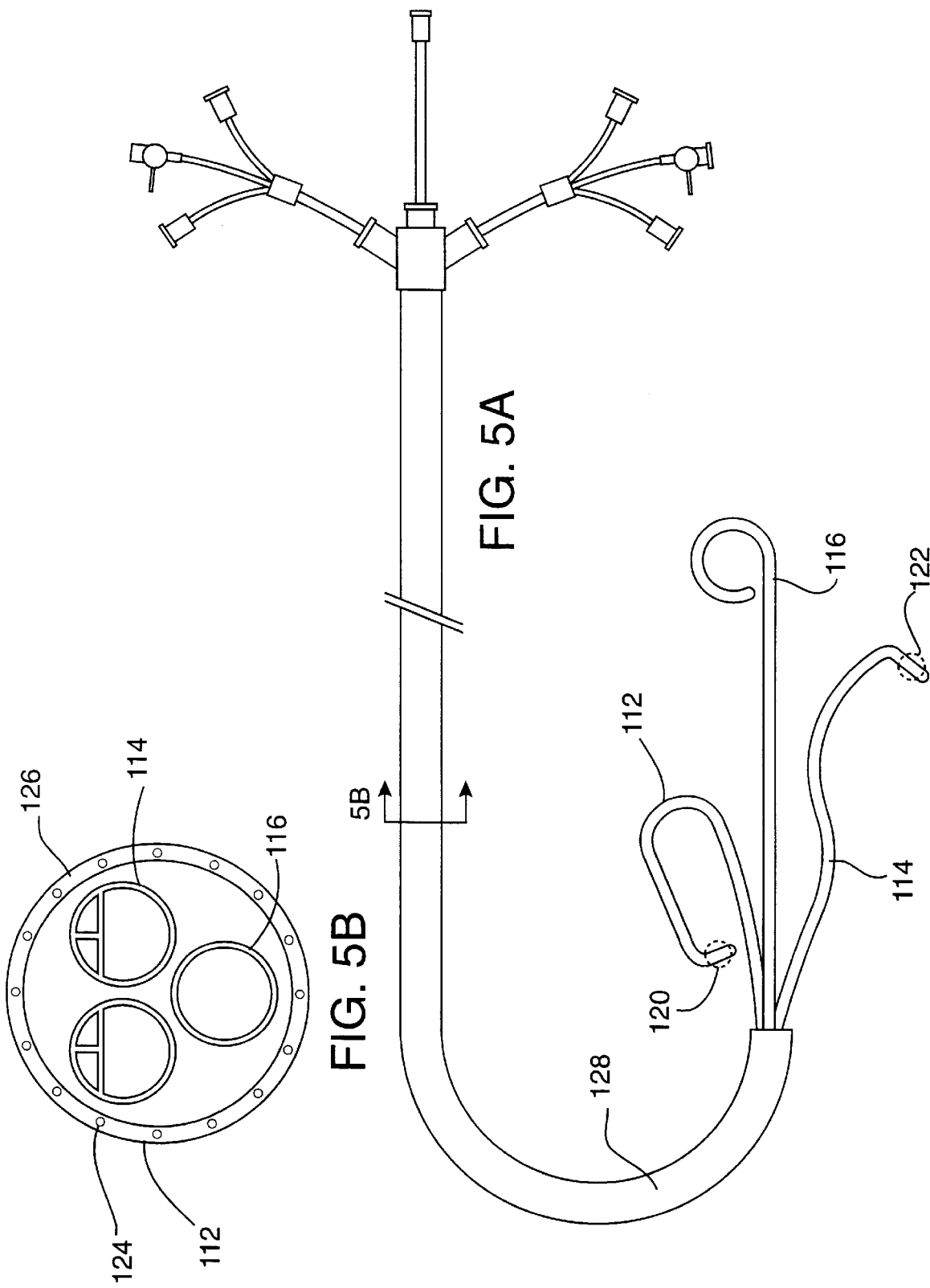

METHOD OF PERFUSING THE CORONARY VASCULATURE

This is a Division of application Ser. No. 08/351,850, filed Dec. 7, 1994 now allowed which is a continuation-in-part of application Ser. No. 08/282,192, filed Jul. 28, 1994 now U.S. Pat. No. 5,584,803.

FIELD OF INVENTION

The present invention relates generally to methods and devices for performing surgical procedures. More particularly, it relates to methods and devices for inducing cardioplegic arrest for myocardial protection during cardiac surgery by direct perfusion of the coronary arteries using a transluminal approach from a peripheral arterial entry point.

BACKGROUND OF THE INVENTION

Myocardial protection is an essential part of almost every cardiac surgery procedure. Many cardiac surgery procedures cannot be effectively performed on a beating heart because the motion of the heart muscle would interfere with the intricate surgical manipulations. Also, for procedures where the coronary arteries or one of the chambers of the heart must be opened, the blood pressure in the beating heart would cause excessive bleeding that would endanger the patient and obscure the surgical site.

For most cardiac surgery procedures, it is preferable to stop the heart from beating for a period of time so that the surgery can be performed. It is extremely important that the heart muscle or myocardium be protected and supported during the time that the heart is stopped so that it does not suffer cellular or nerve damage that would prevent the heart from working properly when it is started again. There are two important aspects to the process of myocardial protection: (1) Reducing the oxygen demand of the heart muscle; and (2) adequately oxygenating the heart muscle and maintaining the proper chemical balance so that cellular damage does not occur. There are two approaches currently used to reduce the oxygen demand of the heart muscle. The first is to stop the heart from beating by cardioplegic arrest. The second is to reduce the temperature of the heart muscle to reduce the oxygen demand, i.e. hypothermia. Currently preferred procedures combine these two approaches in a method known as cold cardioplegia.

Typically, when open heart surgery is performed the chest is opened using a median sternotomy to gain surgical access to the heart. This also allows access to the aorta for cross clamping which is important for standard methods of administering cardioplegia. Before stopping the heart, the patient is prepared by placing an arterial cannula and a venous cannula which are connected to a cardiopulmonary bypass (CPB) system. The CPB system takes over the functions of the heart and the lungs of the patient by pumping and oxygenating the blood while the heart is stopped. Once the CPB system is connected and started, the ascending aorta can be cross clamped to isolate the coronary arteries from the rest of the systemic arterial circulation. Then, cardioplegic arrest is induced by injecting 500–1000 cc of cardioplegic solution into the aortic root using a needle or cannula which pierces the wall of the ascending aorta upstream of the cross clamp. The needle puncture in the aorta must be repaired before the heart is restarted.

When significant insufficiency of the aortic valve exists, aortic root injection of cardioplegia is contraindicated. In these cases it is recommended that the cardioplegic solution be perfused directly into the coronary arteries. An aortotomy incision is first made in the aorta upstream of the cross clamp. One or two coronary perfusion cannule are then inserted into the aorta though the aortotomy incision, then into the coronary arteries. If two cannulae are used, both the right and the left coronary arteries can be perfused simultaneously. If only one cannula is used, the coronaries are perfused serially, usually starting with the left coronary artery because it supplies blood to the greater mass of myocardial tissue. Once the recommended dosage of cardioplegic solution has been injected, the perfusion cannulae are withdrawn. The aortotomy incision must be repaired before the heart is restarted.

For very long surgical procedures, it is recommended that the coronary arteries be reperfused with oxygenated cardioplegic solution or a mixture of oxygenated blood and cardioplegic solution every twenty to thirty minutes to prevent the build up of any oxygen debt in the myocardial tissue and to maintain cardioplegic arrest and hypothermia of the heart. If the perfusion is being done by injection into the aortic root or into the coronary arteries, this usually requires interrupting the surgery while the cardioplegic solution is infused. This lengthens the overall procedure and the amount of time that the patient must be kept on cardiopulmonary bypass.

In recent years another approach has been suggested for administering cardioplegia by retrograde perfusion through the coronary sinus. Typically, a retroperfusion catheter with a balloon cuff on the end is introduced into the right atrium through an atriotomy incision and inserted into the coronary sinus. The balloon is inflated to occlude the coronary sinus and cardioplegic solution is pumped in a retrograde manner through the coronary veins into the capillary bed and eventually out through the coronary arteries. Cardioplegia by retroperfusion has a number of advantages over antegrade perfusion via the aortic root or coronary arteries. First, no punctures or incisions which would have to be repaired at the end of the procedure need to be made in the aortic wall for inserting an aortic root or coronary perfusion cannula. Second, the heart can be intermittently or constantly perfused with cardioplegic solution throughout the procedure without interrupting the surgery. Third, retrograde perfusion is thought to more completely perfuse the heart muscle in the case of occlusive coronary artery disease, effectively delivering cardioplegic solution to myocardial tissue downstream of a tight stenosis or total occlusion that would not be adequately perfused by antegrade injection.

Retroperfusion of cardioplegia is not without its disadvantages. Early experience with retroperfusion showed that the coronary sinus is sensitive to mechanical and pressure injury. The catheter must be carefully placed to avoid injury to the coronary sinus and to avoid occluding the middle cardiac vein with the balloon cuff which would result in incomplete perfusion of the myocardium. Complete perfusion of the myocardium is also not assured when the coronary arteries are highly collateralized. Highly developed collaterals and vascular adhesions to the heart can provide escape routes for the cardioplegic solution before the heart is thoroughly perfused. Veno-venous shunting can be responsible for diverting as much as 40% of the cardioplegic solution before it ever reaches the capillary bed. Moreover, the pressure sensitivity of the coronary sinus necessitates keeping the perfusion pressure under 50 mmHg to avoid pressure injury, whereas the coronary arteries, being smaller in diameter and more muscular, can be safely perfused at pressures up to 150 mmHg. The lower perfusion pressure means that it can take up to thirty minutes to deliver the recommended 500–1000 ml of cardioplegic solution by retrograde perfusion and, consequently, it takes longer to induce cardioplegic arrest. By contrast, usually, only about five minutes are required to deliver the same quantity of solution by antegrade perfusion and cardioplegic arrest is almost immediate.

At least one study has suggested introducing cardioplegia by combining aortic root injection and retrograde coronary sinus perfusion. This method achieves almost immediate cardioplegic arrest with a preliminary bolus of cardioplegic solution into the aortic root, and cardioplegic arrest and hypothermia are then maintained by continuous retrograde coronary sinus perfusion of cold cardioplegic solution. This solves the time delay problems that arise from the slower retrograde perfusion and the interruption of longer surgical procedures for repeated antegrade perfusion. However, by requiring two sets of perfusion cannulae, this procedure introduces additional complications and potentially increases the risk of mechanical injury to the vessels involved. It also does nothing to solve an additional major problem shared by both antegrade and retrograde cardioplegia techniques, that of the necessity to cross clamp the ascending aorta to isolate the coronary arteries from the arterial circulation. The coronary arteries must be isolated to prevent reperfusion of the myocardium with warm oxygenated blood from the CPB system which would wash out the cardioplegic agent and prematurely start the heart beating again. Currently the only well-accepted way to isolate the coronary arteries is by aortic cross clamping. This is not a large problem during most open chest heart surgery where the surgeon has easy access to the ascending aorta. However, when the procedure being performed does not otherwise require opening the chest, the necessity of opening the chest for the sole purpose of placing the aortic cross clamp introduces significant trauma and risk of complication which might be avoided. Also, there are cases in open chest heart surgery where cross clamping of the aorta is contraindicated. These cases include severe calcification of the aortic wall, and extreme scarring and adhesions of the aorta, which can occur for instance, in the case of repeat heart surgery.

Minimally invasive surgery is a very important trend within the field of surgery today. Generally, minimally invasive surgical techniques use endoscopic or transluminal surgical approaches to minimize the trauma and morbidity of surgical procedures. There has been some speculation recently that cardiac surgery could also be performed using minimally invasive surgical techniques. For this to be possible, not only must procedures be developed for performing the surgery through endoscopic or transluminal approaches, but the myocardial protection and cardiopulmonary support must also be performed by minimally invasive techniques. Current methods of administering cardioplegia and establishing cardiopulmonary bypass do not meet this need. All of the accepted methods for inducing cardioplegia, whether by antegrade or retrograde perfusion, still require cross clamping of the aorta to isolate the coronary arteries from the systemic circulation. Even though femoral-to-femoral cardiopulmonary bypass systems have been available for many years, these systems cannot achieve total bypass of the heart without aortic cross clamping to isolate the coronary arteries from the systemic circulation. Consequently, femoral-to-femoral cardiopulmonary bypass systems have mostly been used as support systems for patients at risk during procedures that do not require total cardiopulmonary bypass. The continuing need for invasive aortic cross clamping is a major obstacle to achieving the goal of performing cardiac surgery through minimally invasive surgical techniques.

What is needed, therefore, are methods and devices for inducing cardioplegic arrest, and for isolating the coronary arteries from the systemic circulation to maintain cardioplegic arrest, that can be achieved through minimally invasive surgical techniques. Preferably, the methods and devices should allow these goals be achievable through a transluminal approach from a peripheral arterial access and should require no aortic cross clamping that would necessitate a median sternotomy or other grossly invasive surgical access to the heart. By eliminating the need for aortic cross clamping, such a system would remove one of the major barriers to performing cardiac surgery through minimally invasive surgical techniques. Such a system would also allow total cardiopulmonary bypass using a femoral-to-femoral cardiopulmonary bypass system. Total cardiopulmonary bypass and myocardial protection could then be achieved through a minimally invasive transluminal approach.

SUMMARY OF THE INVENTION

The present invention provides methods, systems and devices for inducing cardioplegic arrest and for isolating the coronary arteries from the systemic circulation to maintain cardioplegic arrest during cardiac surgery. The devices take the form of one or more arterial catheters for introducing cardioplegic solution by direct antegrade perfusion into the coronary arteries and for occluding the coronary ostia so that blood from the systemic circulation cannot enter the coronary arteries. The catheters, when combined with a cardiopulmonary bypass system, create a total cardiopulmonary bypass and myocardial protection system. When a minimally invasive cardiopulmonary bypass system, such as a femoral-to-femoral cardiopulmonary bypass system, is used, total cardiopulmonary support is achieved without the need for grossly invasive surgical access to the heart.

In a first preferred embodiment, the invention provides a single arterial catheter for introduction through a peripheral artery access by arterial cutdown or by the Seldinger technique. The single catheter has at least two distal branches which are adapted for selective intubation and occlusion of each of the coronary ostia. Since there is considerable variability in the normal coronary anatomy of humans, the single catheter can be made in a number of different versions. To accommodate most patients, the single catheter is made with two distal perfusion branches, one each for the: right and left coronary ostia. A second variation with three distal perfusion branches can be made for the occasional patient who has three significant coronary ostia, such as when the left anterior descending coronary artery and the circumflex artery originate separately from the aortic root. For the rare cases in which a patient has all of the coronary arteries arising from a single coronary ostium, a single-ended catheter from one of the embodiments described below can be used.

Preferably, the length and diameter of the catheter are such that they allow the catheter to be introduced via the femoral artery. Alternatively, the catheter can be adapted for introduction from the carotid or brachial artery or from another peripheral arterial access. In one preferred embodiment, each of the distal ends of the catheter have an individually inflatable balloon for engaging and occluding each of the coronary ostia. In alternate embodiments, an O-ring or conically tapered occlusion device can be used in place of each of the inflatable occlusion balloons. Each distal end of the catheter has a through lumen which exits the catheter distal to the occlusion device. The through lumens can extend in parallel through the entire length of the catheter or they can branch from a single perfusion lumen within the proximal shaft of the catheter. The through lumens should have a sufficient internal diameter to allow a flow rate of cardioplegic solution of about 100–200 ml/min or greater with a safe perfusion pressure which does not exceed 150 mmHg at the distal ends of the catheter.

Each distal branch of the catheter can be preshaped to selectively enter one of the coronary ostia. Such preshaped selective curves for coronary catheters are well known in the art and are commonly employed on angiography catheters and angioplasty guiding catheters. Alternatively, each of the distal branches can be individually directed into its respective coronary ostium using a steerable guidewire.

In one alternate embodiment, the catheter may be made with a separate distal branch for venting blood from the left ventricle. This venting branch does not have an occlusion device, but instead has an atraumatic distal tip with one or more vent holes which can be safely passed across the aortic valve to vent blood from the left ventricle through a venting lumen in the catheter. The atraumatic distal tip can have a soft blunt end, a bulbous tip, or a curve such as a pigtail that can cross the valve without damaging it. The venting branch should have a small enough outer diameter that it can be positioned across the aortic valve without rendering it incompetent.

In a second preferred embodiment, the invention provides a system of separate arterial catheters, one for each coronary ostium and, optionally, a separate catheter for venting the left ventricle. Each of the coronary perfusion catheters has an inflatable balloon cuff or other occlusion device at the distal end. A perfusion lumen exits each coronary perfusion catheter distal to the occlusion device. The distal ends of each of the coronary perfusion catheters can be preshaped to selectively enter its respective coronary ostium, or each of the coronary catheters can be individually directed into its respective coronary ostium using a steerable guidewire support system. If the catheters are made with selective coronary curves, the catheter shafts should be reinforced or made rigid enough that they can be manipulated into the coronary ostia using selective catheterization techniques. The venting catheter has an atraumatic distal tip and a port near the distal end that is connected to a venting lumen that runs the length of the catheter. Preferable, the catheters can all be introduced through a single arterial sheath placed in the femoral artery or another peripheral artery by arterial cutdown or by the Seldinger technique. To reduce the number of arterial access ports that need to be made, the arterial sheath can be made integral with the arterial cannula of the cardiopulmonary bypass system. One or more hemostasis valves in the arterial cannula allow the coronary and venting catheters to pass through the blood flow lumen of the arterial cannula without leakage of blood.

In a third preferred embodiment, the invention provides a system of individual arterial catheters which are delivered to the ascending aorta through a single common guiding catheter. The arterial catheters include one catheter for each coronary ostium and, optionally, a separate catheter for venting the left ventricle. The guiding catheter is preferably made with a reinforced shaft to give the system support, and the distal portion of the shaft is preferably curved to hold the distal end of the catheter in the ascending aorta close to the coronary ostia. Since the individual catheters are supported in the aorta by the common guiding catheter, the construction of the individual catheters can be made simpler without reinforcement, possibly reducing the overall expense of the system.

In each embodiment, the coronary perfusion catheters are preferably combined with a cardiopulmonary bypass system to provide total cardiopulmonary support for the patient undergoing heart surgery. A femoral-to-femoral cardiopulmonary bypass system or other minimally invasive system is preferred to reduce the necessity for invasive access to the heart. A perfusion pump, such as a roller pump, or a pressure cuff can be added to the system to pump the cardioplegic solution through the perfusion catheters, or a syringe can be used. One or more syringes filled with saline solution or with radiopaque contrast diluted with saline can be used to inflate the occlusion balloon cuffs on the perfusion catheters. A stopcock attached to each syringe can be used to keep the balloons inflated for the duration of the surgical procedure.

In the preferred method of the invention, the patient is prepared for cardiopulmonary bypass by placing the arterial and venous cannule in a peripheral artery and peripheral vein respectively and connecting the cannulae to the cardiopulmonary bypass system. The coronary perfusion catheters are introduced into a peripheral artery, such as a femoral artery, advanced toward the heart until their ends are in the ascending aorta, and selectively intubated into each of the coronary ostia. If desired, the optional venting catheter should also be placed across the aortic valve at this time. If systemic hypothermia is to be used in conjunction with the cardioplegic arrest, the systemic circulation should be precooled by pumping cooled blood through the entire circulatory system before total bypass is established. This will also lower the temperature of the myocardium. Precooling the myocardium this way will help to make the cold cardioplegia more effective. When the systemic temperature is within the target range, typically 28° C. to 32° C., the occlusion balloon cuffs are inflated in each of the coronary ostia and immediately the oxygenated cold cardioplegic solution is pumped through each of the perfusion lumens at a rate of approximately 100–200 ml/min in each coronary artery. Cardioplegic arrest is almost immediate. When the heart stops beating, the pressure in the aorta will exceed that in the ventricle and the aortic valve will close around the venting catheter. Blood and other fluids may be vented through the venting catheter by gravity or by a negative pressure applied to the vent lumen with a syringe or pump to depressurize the left ventricle.

Once the initial bolus of 500–1000 ml of cardioplegic solution have been infused, the flow rate can be decreased to a constant 25–50 ml/min to maintain the cardioplegic arrest and the hypothermia of the myocardium. Alternatively, the coronary arteries can be periodically reinfused with oxygenated cold cardioplegic solution to avoid either oxygen depletion, or premature rewarming or restarting of the heart. The occlusion balloon cuffs must be kept inflated for the duration of the surgical procedure so that systemic blood does not enter the coronary arteries. If this happens the heart could start beating prematurely, which would interfere with the surgical procedure.

In the preferred method, the cardiac surgery is performed during the period of cardioplegic arrest using minimally invasive techniques through thoracoscopic or transluminal access to the heart. The method can also be used in conjunction with traditional open chest surgical techniques when there is a contraindication to standard cardioplegia administration techniques, such as significant aortic valve insufficiency, or calcification, scarring or adhesions of the ascending aorta.

After the surgical procedure is completed, the systemic circulation can be rewarmed and the occlusion balloon cuffs deflated and withdrawn from the coronary ostia. If desired, a final bolus of oxygenated normothermic blood mixed with cardioplegic solution can be pumped through the perfusion catheters before the occlusion balloon cuffs are deflated to wash out the coronary arteries and prevent reperfusion injury according to the method described by Buckberg et al. in U.S. Pat. No. 5,011,469. When the rewarmed systemic blood enters the coronary arteries, the heart should resume beating spontaneously. If the heart does not restart spontaneously or if it begins beating irregularly, a defibrillation pulse can be applied to the heart to start it beating correctly. The heart is weaned from CPB, and then the perfusion catheters, vent catheter and bypass cannulae can be withdrawn and the cutdowns or percutaneous punctures closed.

BRIEF DESCRIPTION OF THE DRAWINGS

FIG. 1A is a side elevation view of a coronary perfusion catheter for use in the method of the present invention. FIGS. 1B–1E are transverse cross sections of the coronary perfusion catheter of FIG. 1A taken through section lines 1B–1E, respectively. FIG. 1F is a transverse cross section of an alternate construction to FIGS. 1C and 1D. FIG. 1G is a transverse cross section of an alternate construction to FIG. 1E.

FIG. 2A is a side elevation view of a variation of the first embodiment of the coronary perfusion catheter of FIG. 1 with precurved distal ends. FIGS. 2B–2E are transverse cross sections of the coronary perfusion catheter of FIG. 2A taken through section lines 2B–2E, respectively.

FIG. 4A is a side elevation view of a second embodiment of a coronary perfusion catheter system for use in the method of the present invention. FIGS. 4B–4E are transverse cross sections of the coronary perfusion catheter of FIG. 4A taken through section lines 4B–4E, respectively.

FIG. 5A is a side elevation view of a third embodiment of a coronary perfusion catheter system for use in the method of the present invention. FIG. 5B is a transverse cross sections of the coronary perfusion catheter of FIG. 5A taken through section line 5B.

DETAILED DESCRIPTION OF THE INVENTION

Figures 3A, 3B, 3C, 3D, 3E:
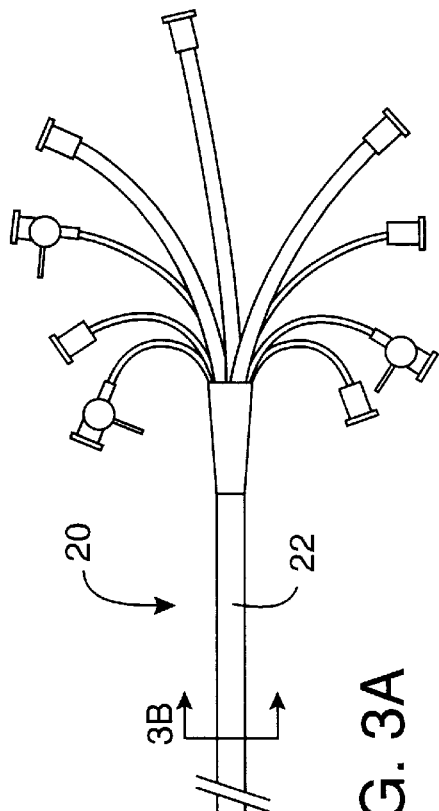
FIG. 3A is a side elevation view of a variation of the first embodiment of the coronary perfusion catheter of FIG. 1.
FIGS. 3B–3E are transverse cross sections of the coronary perfusion catheter of FIG. 3A taken through section lines 3B–3E, respectively.

FIGS. 1A–1E illustrate a first embodiment of the coronary perfusion catheter for use in the method of the present invention. In this embodiment, a single arterial catheter 20 is used to deliver cardioplegic solution to all of the coronary arteries. A side elevation view of the catheter 20 is shown in FIG. 1A. The single catheter 20 has an elongated shaft 22 and a plurality of distal branches 24, 26, 28 which are adapted for selective intubation and occlusion of each of the coronary ostia. In this illustrative example, the catheter includes a first distal branch 24 for engaging the left coronary ostium, and a second distal branch 26 for engaging the right coronary ostium. The catheter is also shown with an optional third distal branch 28 for venting blood from the left ventricle of the heart. All three of the distal branches join together to form a common proximal shaft 22.

The first distal branch 24 of the catheter has a first inflatable occlusion balloon cuff 30 at its distal tip. The balloon 30 communicates with a first balloon inflation lumen 32 which extends through the catheter to a first balloon inflation port 34 on the proximal end of the catheter. A first perfusion lumen 36 extends from a first perfusion fitting 46 at the proximal end of the catheter, through the common proximal shaft 22 and ends at a perfusion port 38 at the distal tip of the first distal branch 24 distal to the first occlusion balloon 30. Optionally, the first branch 24 may also include a first pressure monitoring lumen 40 for monitoring the perfusion pressure in the left coronary artery. The pressure lumen 40 communicates with a first pressure port 42 near the distal tip of the first branch 24 distal to the occlusion balloon cuff 30 and with a first pressure monitoring fitting 44 at the proximal end of the catheter. Alternatively, the perfusion pressure can be monitored by a pressure transducer, such as a piezoelectric transducer, placed in the distal end of the pressure lumen 40. Other sensing devices, such as a thermocouple temperature transducer, could also be added to the catheter for monitoring other physiological conditions.

Likewise, the second distal branch 26 of the catheter has a second inflatable occlusion balloon cuff 50 at its distal tip. The balloon 50 communicates with a second balloon inflation lumen 52 which extends through the catheter to a second balloon inflation port 54 on the proximal end of the catheter. A second perfusion lumen 56 extends from a second perfusion fitting 66 at the proximal end of the catheter, through the common proximal shaft 22 and ends at a perfusion port 58 at the distal tip of the second distal branch 26 distal to the second occlusion balloon 50. Optionally, the second branch 26 may also include a second pressure monitoring lumen 60 for monitoring the perfusion pressure in the right coronary artery. The pressure lumen 60 communicates with a second pressure port 62 near the distal tip of the second branch 26 distal to the occlusion balloon cuff 50 and with a second pressure monitoring fitting 64 at the proximal end of the catheter. The first and second perfusion lumens 36, 56 can run parallel to one another through the common proximal shaft 22, as illustrated in FIG. 1B, or the two distal perfusion lumens 36, 56 can join to form a single common perfusion lumen in the proximal shaft 22 which connects to a single perfusion fitting at the proximal end. The perfusion lumens 36, 56 should have sufficient cross sectional area to allow a flow rate of cardioplegic solution of about 100–250 ml/min or greater with a safe perfusion pressure which does not exceed 150 mmHg at the distal ends of the catheter. A through lumen with an internal diameter of 1.7 mm or an equivalent area will deliver 100 ml/min of blood/cardioplegia mixture or 250 ml/min of crystalloid cardioplegic solution at acceptable perfusion pressures.

The optional third distal branch 28 for venting blood from the left ventricle of the heart has a single venting lumen 68 which connects to a single venting hole 70 or multiple venting holes at the distal tip of the third distal branch 28. The third distal branch 28 is shown in cross section in FIG. 1E. The venting lumen 68 runs the length of the catheter shaft and connects to a venting port 72 at the proximal end of the catheter. The third distal branch 28 has an atraumatic distal tip 74 which can be safely passed across the aortic valve to vent blood from the left ventricle without damaging the leaflets of the valve. In this illustrative example, the venting tip has a pigtail curve 74 for crossing the aortic valve. Other possible configurations for the atraumatic distal tip include a soft blunt end, a bulbous catheter tip or various other atraumatic catheter curves. An alternate construction for the third distal branch 28 is shown in cross section in FIG. 1G. In this variation, the third distal branch 28 has a second lumen 67 for monitoring the blood pressure in the patient's left ventricle. The pressure monitoring lumen 67 would connect one or more pressure monitoring ports near the distal end of the third distal branch 28 to a pressure monitoring fitting at the proximal end of the catheter.

The venting port 72 ends in a Luer fitting or other standard catheter fitting for attaching it to a vacuum collection bottle or roller pump. Each of the perfusion fittings 46, 66 ends in a Luer fitting or other standard catheter fitting for attaching it to a syringe or a perfusion pump. The balloon inflation ports 34, 54 may have a stopcock, as illustrated, or a simple Luer fitting attached at the proximal end for attachment to a syringe or other balloon inflation device.

Preferably, the length and diameter of the catheter are such that they allow the catheter to be introduced via the femoral artery. Alternatively, the catheter can be adapted for introduction from the carotid or brachial artery or from another peripheral arterial access. The length of the catheter is preferably 80–120 cm, 90–100 cm being the preferred length for introduction via a femoral artery. The diameter of each distal branch 24, 26, 28 is preferably 6–7 French (Charrière scale) or 2.0–2.3 mm diameter. The diameter of common proximal portion 22 of the catheter is preferably about 12 French (Charrière scale) or 4.0 mm diameter.

In the embodiment of FIGS. 1A–1E, the straight flexible distal branches 24, 26 of the perfusion catheter 20 are adapted to be directed into the left and right coronary ostia, respectively, using a steerable guidewire introduced through the perfusion lumens 36, 56 or other known selective catheterization technique. FIGS. 2A–2E show a variation of the first embodiment of the coronary perfusion catheter with preshaped curves 76, 78 on each of the distal branches 24, 26 to selectively enter one of the coronary ostia. The first distal branch 24 is illustrated with a Judkins left curve 76 to enter the left coronary ostium, and the second distal branch 26 is illustrated with a Judkins right curve 78 to enter the right coronary ostium.

FIGS. 3A–3E show another variation of the first embodiment of the coronary perfusion catheter. Because it is an anatomical variation for humans to sometimes have three significant coronary ostia rather than two, this variation is made with three distal branches 24, 26, 48, each with an inflatable occlusion balloon cuff and a perfusion lumen which connects to the distal tip of the catheter. The third distal branch 48 is used to selectively intubate the third coronary ostium, which may be a separate origin of the circumflex artery. This illustrative example is shown without the optional distal branch for venting the left ventricle. When this is the case, a separate ventricular venting catheter or a pulmonary artery venting catheter should be used to vent pressure from within the chambers of the heart.

FIGS. 4A–4E show a second preferred embodiment of the invention which provides a system 80 of separate arterial catheters 82, 84, one for each coronary ostium and, optionally, a separate catheter (not shown) for venting the left ventricle. Each of the coronary perfusion catheters 82, 84 has an inflatable balloon cuff 86, 88 or other occlusion device if the distal end. A perfusion lumen 90, 92 exits each catheter distal to the occlusion device. Optionally, each of the perfusion catheters may also include a pressure monitoring lumen 94, 95 for monitoring the perfusion pressure in the coronary arteries. The distal ends of each of the coronary perfusion catheters can be preshaped to selectively enter its respective coronary ostium. Such selective curves for coronary catheters are well known in the art and are commonly employed on angiography catheters and angioplasty guiding catheters. In FIG. 4A the left coronary perfusion catheter 82 is illustrated with a Judkins left curve, and the right coronary perfusion catheter 84 is illustrated with a Judkins right curve. Other common selective curves include Amplatz left and right curves, Sones curves, and specialized curves for selectively catheterizing the proximal anastomoses of coronary bypass grafts. Alternatively, each of the coronary catheters can be individually directed into its respective coronary ostium using a steerable guidewire.

Preferable, the catheters are made with the catheter shafts reinforced with wire braid 98, as illustrated in FIGS. 3C and 3E, to give the catheters sufficient torsional rigidity that they can be manipulated into the coronary ostia using selective catheterization techniques. The diameter of each catheter is preferably 6–7 French (Charrière scale) or 2.0–2.3 mm diameter. Each of the coronary perfusion catheters has a three lumen shaft, as shown in FIGS. 4B and 4D. The balloon inflation lumens 100, 102 communicate with the inflatable occlusion balloon cuffs 86, 88 and the perfusion lumens 90, 92 extend to the distal tips of the catheters distal to the occlusion balloons. A possible alternative construction for the catheter shafts shown in FIGS. 4B and 4D would include a single or double lumen inner shaft with an external or coaxial balloon lumen tube which communicates with the inflatable occlusion balloon cuff. The perfusion lumens of each catheter should have a sufficient internal diameter to allow a flow rate of cardioplegic solution of about 100–250 ml/min or greater with a safe perfusion pressure which does not exceed 150 mmHg at the distal ends of the catheter. A perfusion lumen with an internal diameter of 1.7 mm or an equivalent area will deliver 100 ml/min of blood/cardioplegia mixture or 250 ml/min of crystalloid cardioplegic solution at acceptable perfusion pressures. Preferably, each of the perfusion catheters also includes a third, pressure monitoring lumen 94, 96 for monitoring the perfusion pressure in each of the coronary arteries.

Preferably, the catheters are all introduced through a single arterial sheath 104 placed in the femoral artery or another peripheral artery by arterial cutdown or by the Seldinger technique. To further reduce the number of arterial access ports that need to be made, the arterial sheath 104 can be made integral with the arterial cannula of the cardiopulmonary bypass system, as shown in FIG. 4A. One or more hemostasis valves 106, 108 on the arterial cannula allow the coronary perfusion 82, 84 and venting catheters to pass through the blood flow lumen 110 of the arterial cannula 104 without significant leakage of blood.

FIGS. 5A–5B show a third preferred embodiment of the invention which provides a system of individual arterial catheters which are delivered to the ascending aorta through a single common guiding catheter 118, one catheter for each coronary ostium 112, 114 and, optionally, a separate catheter 116 for venting the left ventricle. Each of the coronary perfusion catheters 112, 114 has an inflatable balloon cuff 120, 122 or other occlusion device at the distal end. A perfusion lumen exits each catheter distal to the occlusion device. Optionally, each of the perfusion catheters may also include a pressure monitoring lumen for monitoring the perfusion pressure in the coronary arteries. The guiding catheter 118 is preferably made with a wire braid 124 reinforced shaft 126, as shown in FIG. 5B, to give the system support. The distal portion of the shaft is preferably curved to hold the distal end 128 of the catheter in the ascending aorta close to the coronary ostia. Since the individual catheters are supported in the aorta by the common guiding catheter 118, the construction of the individual catheters 112, 114 can be made simpler without reinforcement, as shown in cross section in FIG. 5B.

Figure 6:
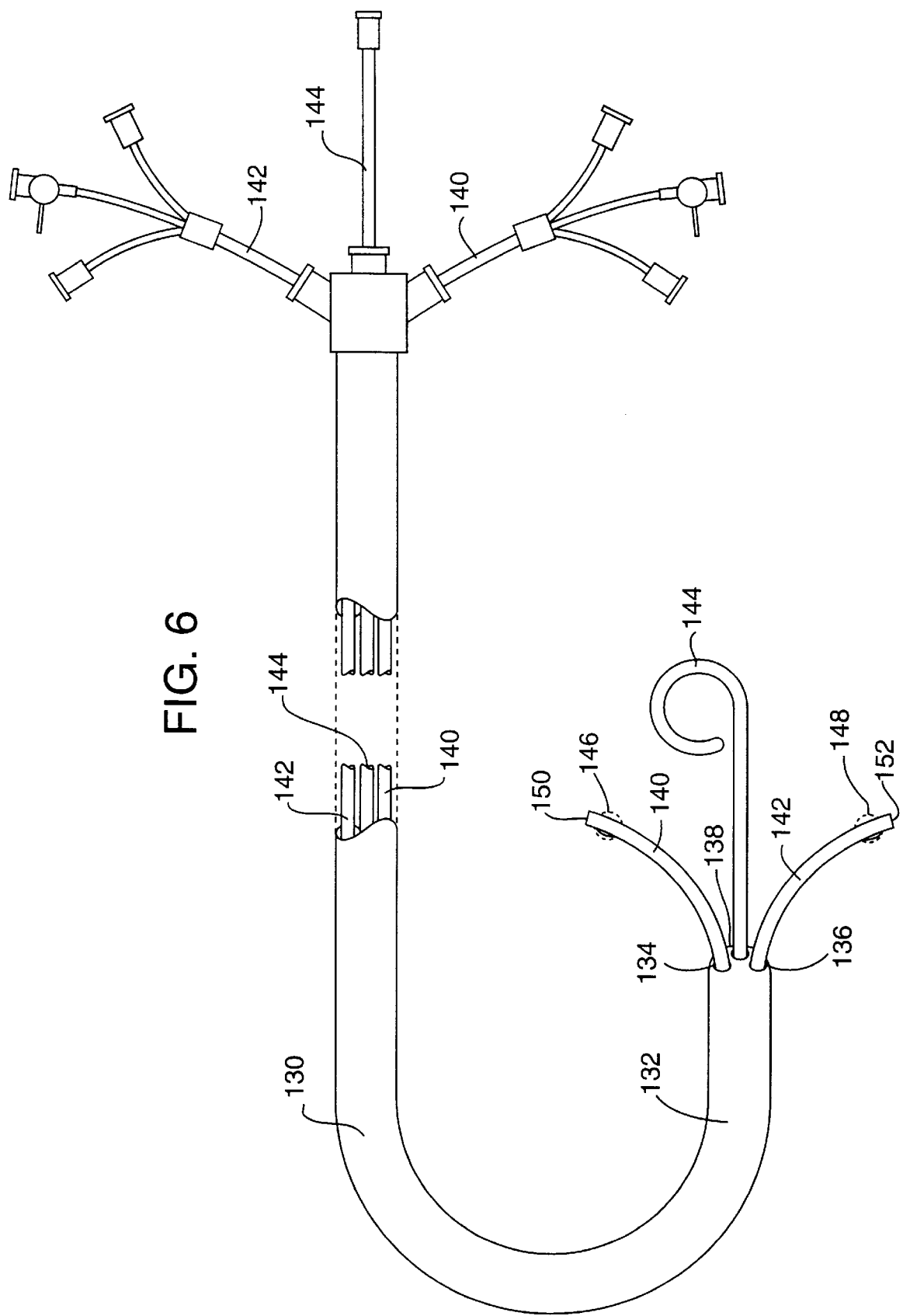
FIG. 6 shows a fourth embodiment of a coronary perfusion catheter system for use in the method of the present invention.

FIG. 6 shows a fourth preferred embodiment of the invention which provides a system of individual arterial catheters which are delivered to the ascending aorta through a multilumen guiding catheter 130. The distal portion 132 of the multilumen guiding catheter 130 is curved to hold the distal end of the catheter in the ascending aorta proximate the coronary ostia in the aortic root. A first coronary perfusion catheter 140 is introduced through a first internal lumen of the multilumen guiding catheter 130. The first lumen of the guiding catheter terminates in a first exit port 134 which is angled to direct the perfusion catheter toward the left coronary artery. A second coronary perfusion catheter 142 is introduced through a second internal lumen of the multilumen guiding catheter 130. The second lumen of the guiding catheter terminates in a second exit port 136 which is angled to direct the perfusion catheter toward the right coronary artery. Each of the coronary perfusion catheters has an inflatable balloon cuff 146, 148 or other occlusion device at the distal end. A perfusion lumen 150, 152 exits each catheter distal to the occlusion device. Optionally, each of the perfusion catheters may also include a pressure monitoring lumen for monitoring the perfusion pressure in the coronary arteries. Optionally, a venting catheter 144 is introduced through a third internal lumen of the multilumen guiding catheter 130. The third lumen of the guiding catheter terminates in a third exit port 138 which is angled to direct the venting catheter 144 across the aortic valve into the left ventricle.

Figures 10A, 10B:
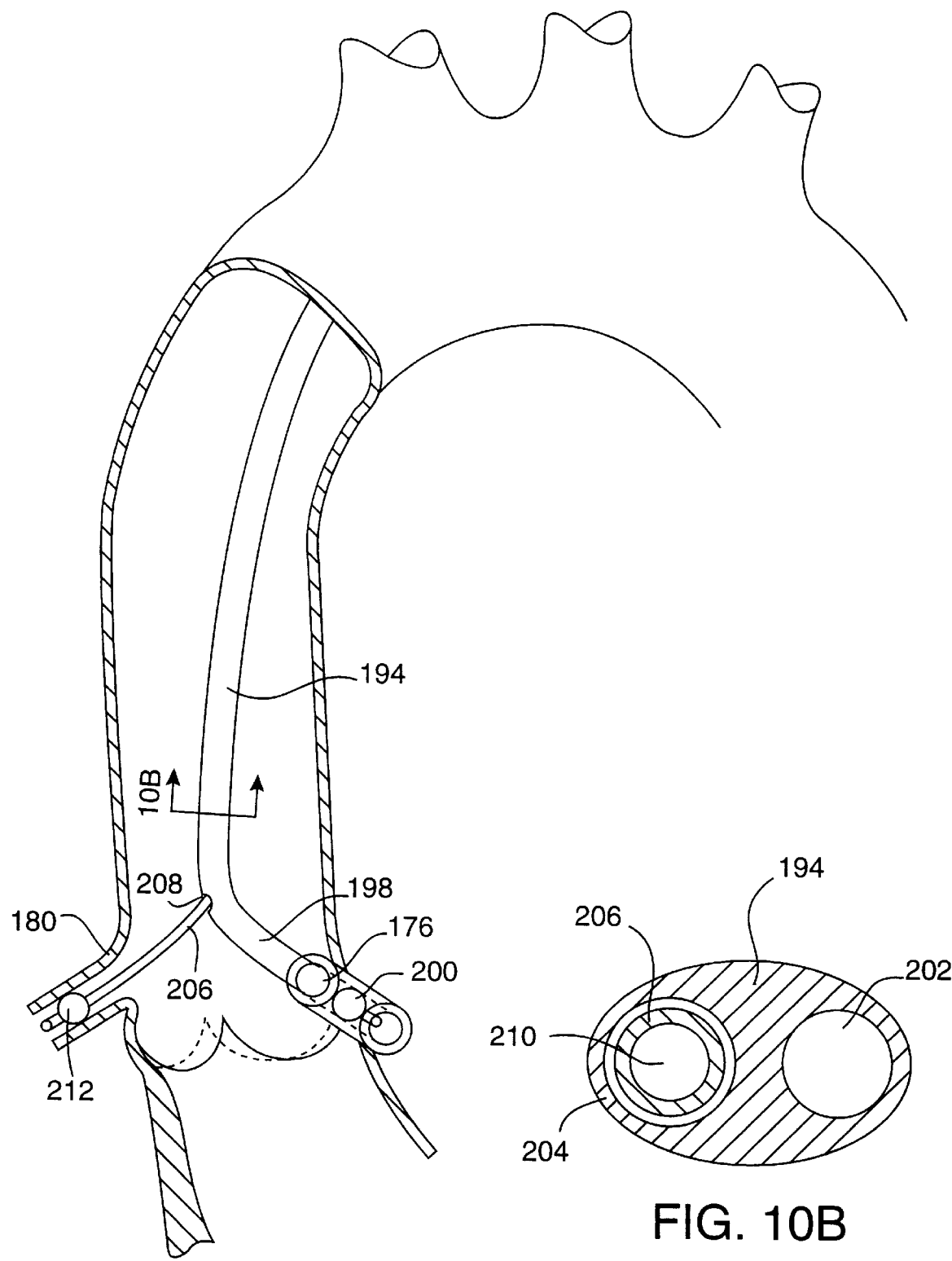
FIG. 10A shows a fifth embodiment of a coronary perfusion catheter system for use in the method of the present invention.
FIG. 10B is a transverse cross section of the coronary perfusion catheter system of FIG. 10A taken through section lines 10B.

FIG. 10A shows a fifth preferred embodiment of the invention which provides a catheter system including a multilumen combination guiding catheter and perfusion catheter 194 and at least one coaxial perfusion catheter 206 delivered through one of the guiding catheter lumens. The distal portion 198 of the multilumen guiding catheter 194 is curved to direct an occlusion device 200 on the distal tip of the guiding catheter into a first coronary ostium, which in this illustrative example is the left coronary ostium 176. The multilumen guiding catheter 194 is shown in cross section in FIG. 10B. The guiding catheter 194 has at least two lumens: a perfusion lumen 202 connecting to the distal tip of the catheter for delivering cardioplegic solution into the first coronary artery, and a guiding lumen 204 for guiding a separate coaxial coronary perfusion catheter 206 to the ascending aorta and into the second coronary ostium 180. In addition, the guiding catheter 194 may also include a separate inflation lumen and/or pressure monitoring lumen, as described in the previous embodiments.

The coronary perfusion catheter 206 is introduced through the guiding lumen 204 of the multilumen guiding catheter 194, and it exits the guiding catheter through a side port 208 which is positioned within the ascending aorta. An occlusion device 212 on the distal end of the coronary perfusion catheter 206 is directed into the second coronary ostium, in this case the right coronary ostium 180, by an appropriately curved distal end or by using a guidewire. The coronary perfusion catheter 206 has at least one internal lumen 210, as shown in FIG. 10B, for delivering cardioplegic solution into the second coronary artery. The coronary perfusion catheter 206 may also include additional lumens for inflation and/or pressure monitoring.

Alternatively, if a separate guide lumen 202 is not provided in the guiding catheter 194, the coronary perfusion catheter 206 can be introduced through the perfusion lumen 202 of the guiding catheter 194, and the coronary perfusion catheter 206 can be adapted to seal against the side port 208 of the guiding catheter 194. The distal portion of the coronary perfusion catheter 206 can be tapered so that it seals against the side port 208 as it is advanced out of the guiding catheter 194. In addition, a sealing means such as an O-ring seal can be provided in the side port 208. In this configuration, the guiding catheter 194 and the coronary perfusion catheter 206 can be perfused separately through their respective lumens, or the flow channels can be joined by placing one or more holes through the sidewall of the coronary perfusion catheter 206 proximal to were it exits the side port 208 so its perfusion lumen 210 communicates with the perfusion lumen 202 of the guiding catheter 194.

Figure 11:
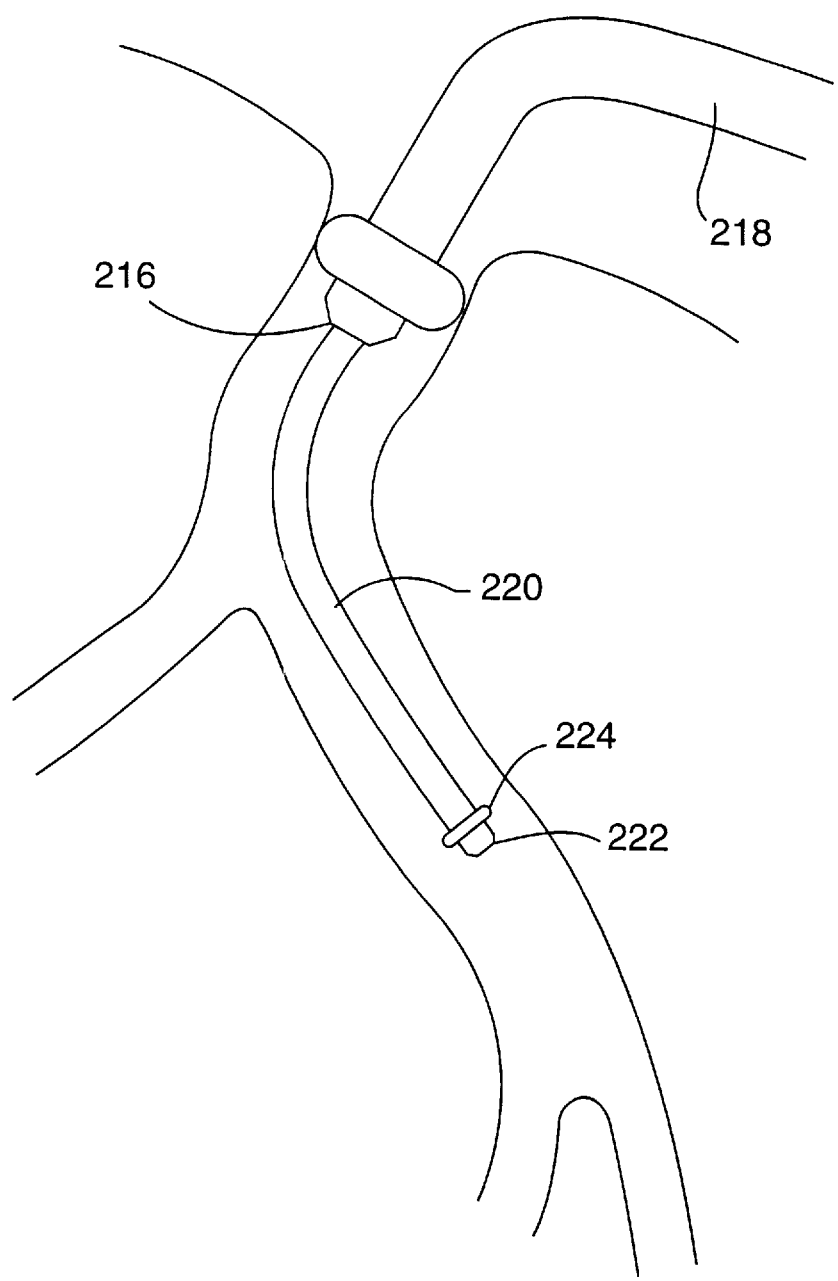
FIG. 11 shows a subselective catheter and coronary artery probe for use with the coronary perfusion catheter system of the present invention.

FIG. 11 shows a subselective catheter and coronary artery probe 220 that can be used in conjunction with the coronary perfusion catheter system of the present invention. The subselective catheter 220 is dimensioned so that it can be delivered to the coronary arteries through one of the perfusion lumens 216 of the perfusion catheter system 218. The subselective catheter 220 can be used for subselectively delivering cardioplegic solution to one of the branches of the coronary arteries or for infusing therapeutic agents, such as thrombolytic drugs, into the coronary arteries while the heart is arrested. The distal tip 222 of the subselective catheter 220 also serves as a coronary artery probe for helping to locate stenoses or occlusions in the coronary arteries. The distal tip 222 of the subselective catheter 220 is advanced selectively into the coronary artery and its branches until it is stopped by a blockage in the artery. The distal tip 222 is configured to have a small bulbous ring 224 which can be palpated through the walls of the coronary artery to help the surgeon to locate the stenoses and to pick the appropriate site for graft anastomosis during bypass surgery. During open chest bypass surgery, the ring 224 can be palpated directly by the surgeon with a gloved hand. During closed-chest thoracoscopic bypass surgery, an elongated handheld probe introduced through an access port in the patient's chest can be used for locating the small bulbous ring 224 on the catheter tip 222. Preferably, the ring 224 is made of metal or of plastic with a radiopaque filler so that the distal probe tip 222 of the catheter 220 can also be located fluoroscopically.

Another use of the coaxially placed subselective catheter and coronary artery probe 220 is to create a recirculating heat exchanger circuit within the coronary arteries themselves to increase the effectiveness of the tissue cooling in cold cardioplegia methods. In this alternative method, one of the catheters, for example the subselective catheter 220, is used to infuse cold cardioplegic solution into the coronary arteries at a higher rate than would otherwise be necessary to establish cardioplegic arrest. The other catheter, in this case the perfusion catheter 218, is used to vent the excess cardioplegic fluid so that the pressure in the coronary artery does not exceed the desired perfusion pressure. The advantage of this method is that it increases the flow rate of cold cardioplegic solution which is pumped through the coronary arteries to better cool the cardiac tissue without increasing the perfusion pressure or pumping an excessive amount of cardioplegic solution through the patient's capillary bed. This method will be especially beneficial in the performance of closed-chest cardiac procedures where it would be inconvenient to bath the entire heart in cold saline solution or to wrap a heat exchanger around the outside of the heart.

Figure 7A:
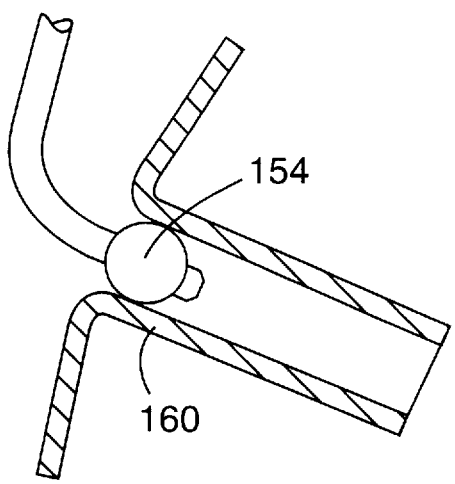
FIGS. 7A–7F show the tip of the coronary perfusion catheter with six alternative embodiments of the occlusion means for blocking blood flow into the coronary arteries.

FIGS. 7A–7F illustrate alternative occlusion means for the distal tip of the coronary perfusion catheters. FIG. 7A illustrates an inflatable occlusion balloon cuff 154 as previously described. Preferably the occlusion balloon 154 is approximately spherical when inflated. The maximum diameter of the inflated balloon 154 can be about 5 mm, which is sufficient to occlude the coronary ostia 160 in most patients. Occlusion balloons as large as 7 or 8 mm may occasionally be needed for occluding vein grafts which exceed 5 mm internal diameter. The balloon is preferably made from an elastomeric material such as latex, silicone or polyurethane or a blend of materials such as polyurethane and polyvinyl chloride. The balloon can be adhesively bonded and/or tied to the catheter shaft. If a thermoplastic elastomer is used as the balloon material, the balloon can be heat bonded directly to a shaft of compatible material without adhesives. Using an elastomeric balloon material allows the deflated balloon to achieve an almost zero deflated profile and it makes the balloons somewhat self deflating from the elastic energy stored in the balloon material on inflation. The balloon inflation pressure should be slightly higher than the maximum perfusion pressure that will be used to prevent migration of the balloon and to prevent cardioplegic solution or systemic blood from leaking past the inflated balloon. At the same time, the inflation pressure should be low enough that the inflated balloon does not inadvertently dilate the coronary ostia. An inflation pressure of 350 mmHg has been shown to be effective. The inflatable occlusion balloon cuff occludes the coronary artery very gently with very little danger of damaging the ostium. Additional features, such as ribs or bumps, may be molded into the surface of the balloon to increase the friction with the coronary ostia to prevent slippage of the balloon without increasing the inflation pressure.

Figure 7B:
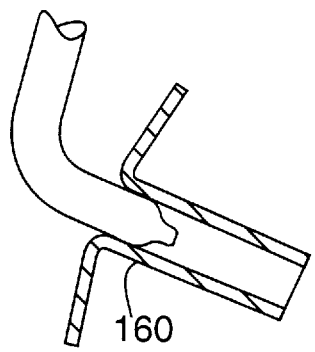
Figure 7C:
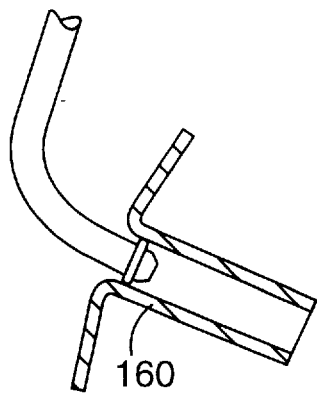

FIG. 7B shows a coronary perfusion catheter tip 156 with a conically tapered occlusion means 158 at the distal tip. This conical occlusion means 158 is wedged into the coronary ostium 160 to occlude the flow around the catheter tip. FIG. 7C shows a coronary perfusion catheter tip with an O-ring occlusion 162 means at the distal tip. The O-ring occlusion means 162 is, likewise, wedged into the coronary ostium 160 to occlude the flow around the catheter tip. With these two alternate occlusion means, care must be taken to size the catheter tip appropriately for the coronary ostium so that a reliable seal can be achieved without damaging the tissue around the ostium.

Figure 7D:
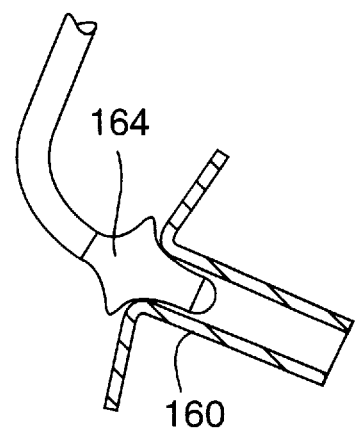
Figure 7E:
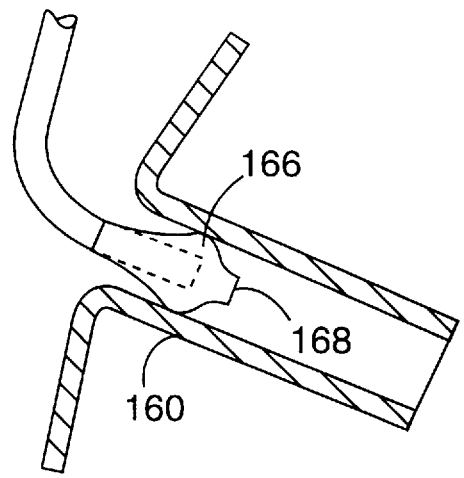
Figure 7F:
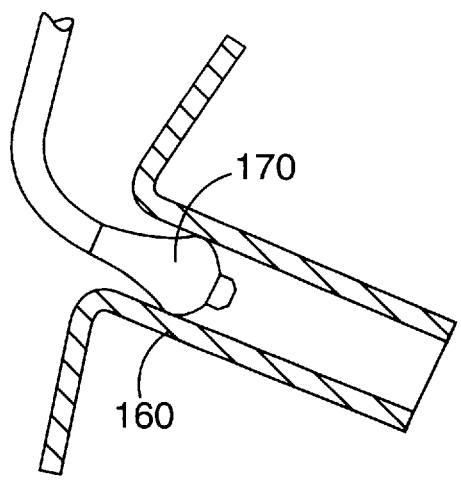

FIG. 7D shows a coronary perfusion catheter tip with a wedge-shaped occlusion means 164 at the distal tip. The wedge 164 is sized to occlude the coronary ostium 160 and isolate the coronary artery from the systemic blood flow. The wedge 164 can be made from a solid or hollow, molded plastic or elastomeric material, or the wedge can be formed as a shaped occlusion balloon which achieves the wedge shape when inflated. FIGS. 7E and 7F show reverse wedge-shaped occlusion balloons 166, 170. The balloons 166, 170 are preferably formed as shaped occlusion balloons which achieve the reverse wedge shape when inflated. The reverse wedge shape is designed to hold the occlusion balloon in the coronary ostium 160 and to discourage dislodgment. FIG. 7E illustrates a variation of the occlusion balloon 166 which is self-inflating. When cardioplegic solution is infused through the perfusion lumen of the catheter, it first enters the occlusion balloon 166 which is bonded near the distal end of the catheter. The pressure of the cardioplegic solution inflates the balloon 166 and seals the sides of the balloon against the walls of the coronary ostium 160. The cardioplegic solution exits the occlusion balloon 166 through a distal orifice 168 into the coronary artery. The distal orifice 168 offers a slight resistance to the flow of the cardioplegic solution which pressurizes the occlusion balloon 166 and keeps it inflated as long as there is sufficient flow of cardioplegic solution through the catheter.

For the embodiments of the occlusion means shown, in FIGS. 7B–7E, that do not require an inflation lumen the construction of the perfusion catheter can be much simpler than for the occlusion balloon embodiments previously described. A cross section of one possible embodiment of the shaft construction is shown in FIG. 1F. The perfusion catheters (or the distal branches of a single perfusion catheter) 24 have a perfusion lumen 36 and a pressure monitoring lumen 40 which connect the proximal and distal ends of the catheter. If other means are provided to monitor and control the perfusion pressure in the coronary arteries, the catheters can be further simplified with a single perfusion lumen from end to end, which could lower the overall cost of the catheter system and the overall diameter of the catheters.

The catheter system of the present invention is preferably supplied to the end user in a sterile ready to use condition. For embodiments of the system that employ multiple catheters, guidewires, guiding catheters and/or sheaths and cannulae, all of the components necessary for carrying out the procedure may be packaged together in a single kit sterilized and ready for use.

Figure 8:
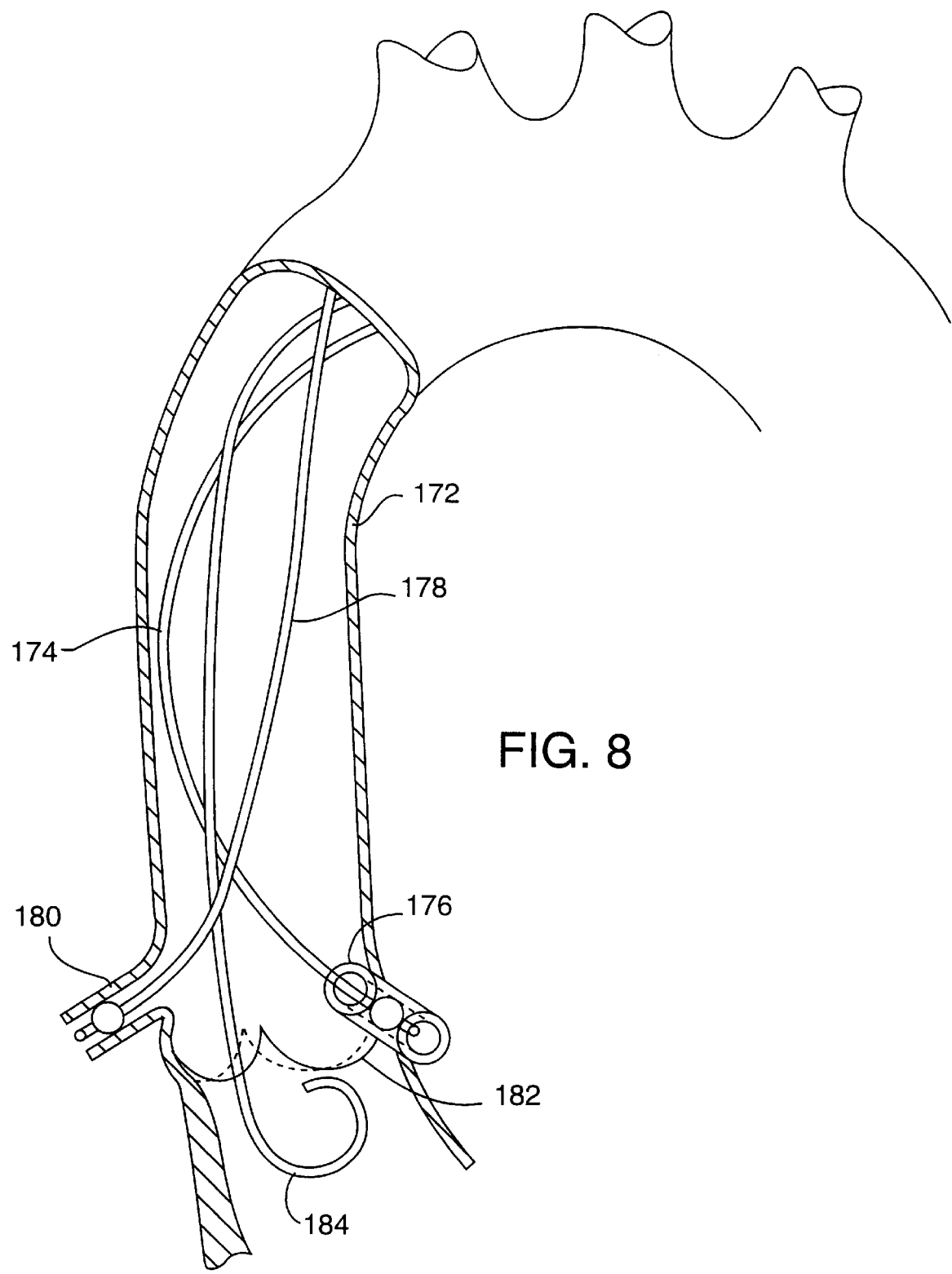
FIG. 8 is a diagram of the ascending aorta showing the placement of two coronary perfusion catheters and the left ventricular vent catheter.

FIG. 8 is a diagram of the ascending aorta 172, showing the placement of the coronary perfusion catheters 174, 178 and the left ventricular venting catheter 184. A first coronary perfusion catheter 174 engages the left coronary ostium 176, and a second coronary perfusion catheter 178 engages the right coronary ostium 180. Placement of the catheters is generally done under fluoroscopic guidance. In order to improve the fluoroscopic visualization of the catheters, the catheter can be provided with one or more radiopaque marker rings of a dense material, such as gold, platinum, tantalum or tungsten, at their distal tips. Alternatively, or in addition, the catheter shafts may be made of a polymer compounded with a radiopaque material, such as barium or bismuth compounds, to increase the radiopacity.

The perfusion catheters 174, 178 can be placed with fluoroscopic guidance by either of two methods. In the first method, the distal ends of the catheters are preshaped with selective coronary curves. The curves are straightened out with a stiff guidewire placed in the perfusion lumen, as shown by phantom lines 82', 84' in FIG. 4A, when the catheters are introduced into the femoral artery and advanced through the descending aorta and into the ascending aorta. When the guidewires are withdrawn the catheters resume their curved shapes which are adapted to be easily maneuvered into the coronary ostia. In the second method, the distal ends of the catheters are not precurved, but a curved steerable guidewire is used to direct each of the catheters into the respective coronary ostium. With the third embodiment of the catheter system, illustrated in FIGS. 5A–5B, the curved guiding catheter can assist the steerable guidewire in directing the perfusion catheters to their respective coronary ostia. Alternatively, the lumens of the guiding catheter can be adapted to direct the perfusion catheters into the ostia, as illustrated in FIG. 6.

The perfusion catheters should be inserted far enough into the coronary ostia so that the balloons will be entirely within the coronary arteries when they are inflated. At the same time, the balloons must be positioned upstream of any side branches of the coronary arteries to insure complete isolation of the myocardium from the systemic circulation and complete perfusion of the coronary arteries with cardioplegic solution. Positioning the tip of each catheter about 3 to 5 mm downstream of the coronary ostium prior to inflation will result in correct balloon placement in most cases. Once the catheters are correctly situated, inflating the occlusion balloon cuffs will block all flow into the coronary arteries except through the perfusion lumina of the catheters. The occlusion balloons are preferably inflated with sterile saline solution, or with a mixture of saline and a radiopaque contrast agent, to eliminate any danger of air embolization in the occurrence of a balloon leak or rupture. The positions of the occlusion balloons should be verified fluoroscopically after inflation.

Figure 9:
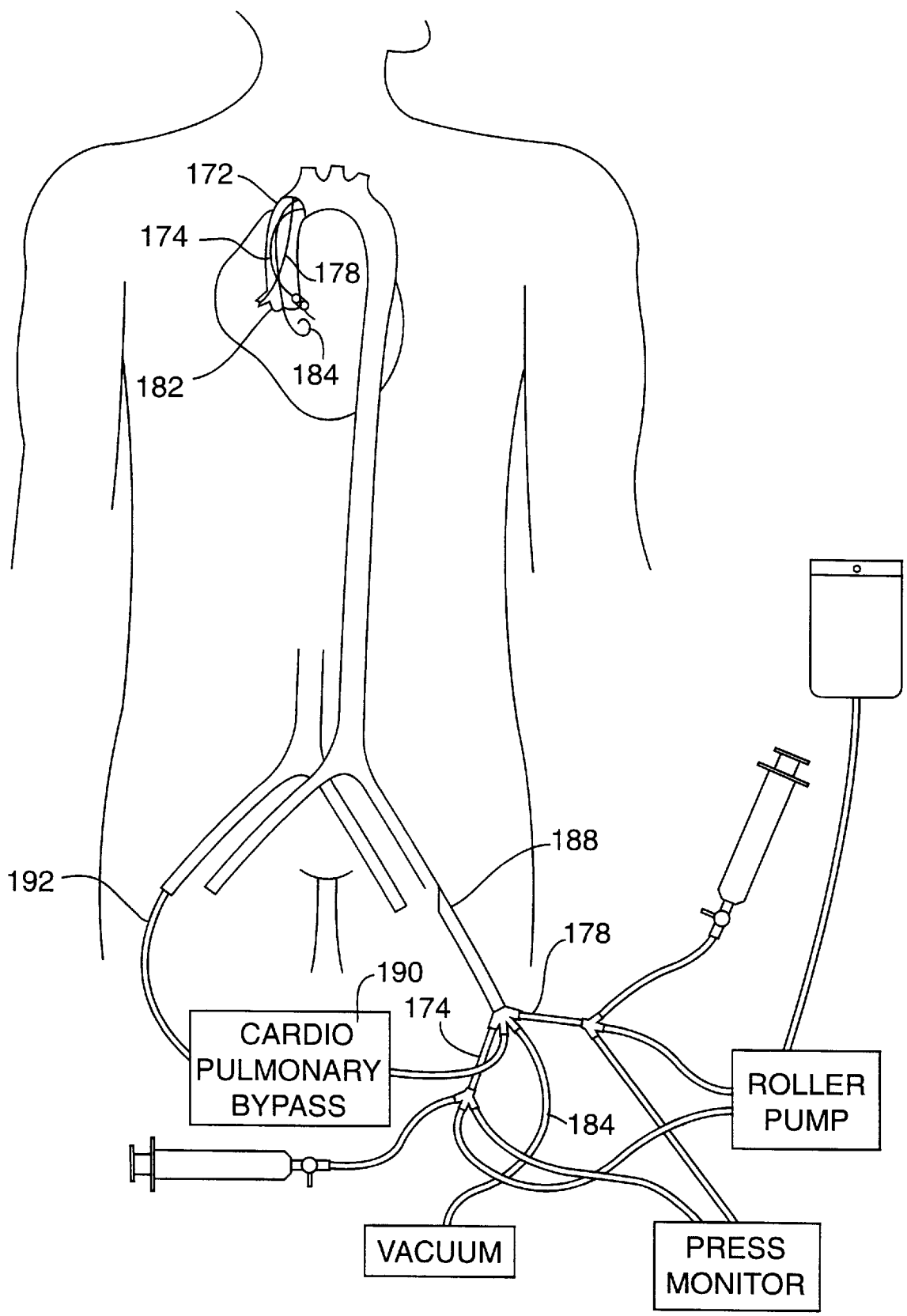
FIG. 9 is a schematic diagram of the complete cardioplegia and cardiopulmonary bypass system for carrying out the method of the present invention.

FIG. 9 is a schematic diagram of the complete cardioplegia and cardiopulmonary bypass system for carrying out the method of the present invention. First, the patient is prepared for cardiopulmonary bypass by placing the arterial cannula 188 in a peripheral artery, such as the femoral artery and venous cannula 192 in a peripheral vein, such as the femoral vein, and connecting them to the cardiopulmonary bypass system 190. A femoral-to-femoral cardiopulmonary bypass system or other minimally invasive system is preferred to reduce the necessity for invasive surgical access to the heart. Examples of suitable femoral-to-femoral cardiopulmonary bypass systems can be found in U.S. Pat. Nos. 4,540,399 and 5,011,469, the specifications of which are hereby incorporated by reference in their entirety. Meanwhile, the coronary perfusion catheter or catheters 174, 178, depending on which embodiment of the invention is employed, are introduced into a peripheral arterial access site, such as a femoral artery, by arterial cutdown or by the Seldinger technique, then directed to the coronary ostia using one of the various techniques described above. If desired, the optional venting catheter 184 should also be placed across the aortic valve 182 at this time.

In the preferred method, the system is used to administer cold cardioplegia to the patient for maximal protection of the myocardium. The cardioplegic fluid preferably consists of an aqueous KCl solution mixed with oxygenated blood at a ratio of four parts blood to one part KCl solution. The aqueous KCl solution consists of crystalloid KCl mixed with saline to have a concentration in the range of 10–50 mEq $K^+$/liter, preferably 15–30 mEq $K^+$/liter. Alternatively, an aqueous KCl solution with a concentration in the range of 10–30 mEq $K^+$/liter, without a blood component, may be used. A comprehensive description of cardioplegic techniques suitable for use in the method of the invention is found in Buckberg, *Strategies and logic of cardioplegic delivery to prevent, avoid, and reverse ischemic and reperfusion damage,* J. Thorac. Cardiovasc. Surg. 1987;93:127–39. If systemic hypothermia is to be used in conjunction with the cardioplegic arrest, the systemic circulation should be precooled by pumping cooled blood through the entire circulatory system before total bypass is established. This will lower the temperature of the patient's body as well as the myocardium, reducing the oxygen demand. Precooling the myocardium this way will also help to make the cold cardioplegia more effective. When the systemic temperature is within the target range, typically between 28° C. and 32° C., the occlusion balloon cuffs are inflated in each of the coronary ostia and immediately oxygenated cold cardioplegic solution, typically between 3° C. and 10° C., is pumped through each of the perfusion lumens at a rate of approximately 100–200 ml/min in each coronary artery. The perfusion pressure in the coronary arteries can be monitored through the pressure monitoring lumens to be sure that the perfusion pressure does not exceed 150 mmHg at the distal ends of the catheters. The pump pressure should not exceed 350 mmHg to avoid undue hemolysis in the blood component of the fluid mixture. If a cardioplegic solution without any blood component is used, a higher pump pressure may be used. However, the actual perfusion pressure in the coronary arteries should not be allowed to exceed 150 mmHg to avoid endothelial damage to the arterial walls.

Cardioplegic arrest occurs almost immediate when the cardioplegic solution is infused. When the heart stops beating, the pressure in the aorta will exceed that in the ventricle and the aortic valve will close around the venting catheter. The venting catheter can be vented by gravity or a negative pressure can be applied to the vent lumen with a syringe or pump to depressurize the left ventricle. If desired, the venting catheter can be connected to a blood recovery unit which reprocesses the blood and adds it to the bypass circuit.

An initial bolus totaling 500–1000 ml of cardioplegic solution is infused into the coronary arteries. After the initial bolus, the flow rate can be decreased to a constant 25–50 ml/min to maintain the cardioplegic arrest and the hypothermia of the myocardium. Alternatively, the coronary arteries can be periodically reinfused with oxygenated cold cardioplegic solution to avoid either oxygen depletion or premature restarting of the heart. The occlusion balloon cuffs must be kept inflated for the duration of the surgical procedure so that systemic blood does not enter the coronary arteries. If this happens the heart could start beating prematurely, which would interfere with the surgical procedure.

In an alternative approach, the method of the present invention can be used in conjunction with retrograde perfusion through the coronary sinus to maintain hypothermia and cardioplegic arrest. In this alternative method, the initial bolus of cardioplegia is infused through the coronary perfusion catheters into the coronary arteries. After cardioplegic arrest has been achieved, the balloon of a retrograde perfusion catheter is inflated in the coronary sinus and further cardioplegic solution is perfused retrograde through the coronary circulation at a lower flow rate. The occlusion balloon cuffs are kept inflated to isolate the coronary arteries from the systemic blood circulation, and the cardioplegic solution is vented from the coronary arteries through the perfusion lumens of the coronary perfusion catheters.

In the preferred method, the cardiac surgery is performed during the period of cardioplegic arrest using minimally invasive techniques through thoracoscopic or transluminal access to the heart. The method can also be used in conjunction with traditional open chest surgical techniques when there is a contraindication to standard cardioplegia administration techniques, such as significant aortic valve insufficiency or calcification, scarring or adhesions of the ascending aorta.

In another alternate method, the coronary perfusion catheters of the cardioplegia system can be used as guiding catheters for performing catheter based interventional procedures in the coronary arteries of the patient. In this way, angioplasty, atherectomy, thrombolysis or other interventional procedures can be performed by inserting the interventional catheters through the perfusion lumens of the coronary perfusion catheters into the coronary arteries. Catheter based interventional procedures can thus be combined with minimally invasive cardiac surgery to improve patient outcome.

In yet another alternate method, the coronary perfusion catheters of the cardioplegia system and the method of administering cardioplegia can be used in conjunction with a laser system for transmyocardial revascularization such as any of the systems described in U.S. Pat. Nos. 4,658,817, 5,125,924 and 5,125,926, the specifications of which are hereby incorporated by reference in their entirety. The laser devices can be introduced thoracoscopically or transluminally to maintain the minimally-invasive character of the procedure. The use of these systems in conjunction with the present system of achieving cardioplegic arrest solves the difficulties of applying laser energy to the beating heart described in each of the patents. Namely, performing transmyocardial revascularization on a still heart insures that the laser energy will be applied to the myocardium when it is in the relaxed state, which has been shown to yield better results. It also avoids the possible complication of inducing ventricular fibrillation which can occur when laser energy is applied to the myocardium while it is contracting during systole. The laser induced channels can be more carefully placed while the heart is still so that the ischemic myocardium can be more effectively revascularized and critical structures, such as nerves or coronary arteries, can be carefully avoided with the laser.

After the surgical procedure is completed, the systemic circulation can be rewarmed and the occlusion balloon cuffs deflated and withdrawn from the coronary ostia. If desired, a final bolus of oxygenated normothermic blood mixed with cardioplegic solution can be pumped through the perfusion catheters before the occlusion balloon cuffs are deflated to wash out the coronary arteries and prevent reperfusion injury according to the method described by Buckberg et al. When the rewarmed systemic blood enters the coronary arteries, the heart should resume beating spontaneously. If the heart does not restart spontaneously or if it begins beating irregularly, a defibrillation pulse can be applied to the heart to start it beating correctly. The perfusion catheters, vent catheter and bypass cannulae can now be withdrawn and the cutdowns or percutaneous punctures closed.

Thus, it can be seen that the methods and devices described herein provide a system for inducing cardioplegic arrest and total cardiopulmonary support entirely through minimally invasive transluminal access. The present invention therefore provides an important link in making minimally invasive cardiac surgery a real possibility.

While the above is a complete description of the preferred embodiments of the invention, various alternatives, modifications and equivalents may be used. Therefore, the above description should not be taken as limiting the scope of the invention, which is defined by the appended claims.

What is claimed is:

1. A method of inducing cardioplegic arrest in a heart of a patient, the heart having a coronary vasculature, comprising the steps of:
   a) introducing at least one distal end of at least one perfusion catheter into a peripheral artery of said patient;
   b) advancing said distal end of said perfusion catheter from said peripheral artery into at least one coronary ostium of a coronary artery communicating with said coronary vasculature of said patient;
   c) occluding said coronary ostium of the coronary artery with an occlusion device mounted to said perfusion catheter;
   d) arresting the heart.

2. The method of claim 1, wherein step d) comprises the substep of infusing a cardioplegic agent through a lumen of said perfusion catheter into said coronary vasculature downstream of said occlusion device.

3. The method of claim 2 wherein said cardioplegic agent is infused through said lumen of said perfusion catheter at a rate of at least approximately 100 ml/min at a pump pressure not exceeding 350 mmHg.

4. The method of claim 1, wherein step d) comprises the substep of infusing a mixture of oxygenated blood and a cardioplegic agent through a lumen of said perfusion catheter into said coronary vasculature downstream of said occlusion device at a rate of at least approximately 100 ml/min at a pump pressure not exceeding 350 mmHg.

5. The method of claim 1, further comprising the step of:
   e) isolating said coronary vasculature from systemic circulation of said patient by continuing to occlude said coronary ostium with said occlusion device while the heart is arrested.

6. The method of claim 5, further comprising the step of:
   f) maintaining systemic circulation of said patient with peripheral cardiopulmonary bypass.

7. The method of claim 6, wherein step f) comprises:
   positioning an arterial cannula in a peripheral artery of said patient;
   positioning a venous cannula in a peripheral vein of said patient;
   withdrawing venous blood from said patient through a blood flow lumen in said venous cannula;
   infusing oxygenated blood into said patient through an infusion lumen in said arterial cannula.

8. The method of claim 1, further comprising the steps of:
   g) introducing a venting lumen through an aortic valve of said heart of said patient;
   h) venting a left ventricle of said heart by withdrawing fluid through the venting lumen.

9. The method of claim 1, wherein step a) comprises introducing a single perfusion catheter having at least two distal ends into said peripheral artery of said patient; step b) comprises advancing said at least two distal ends into at least two coronary ostia; step c) comprises occluding each of said at least two coronary ostia with an occlusion device proximate each of said at least two distal ends, respectively; and step d) comprises infusing a cardioplegic agent through at least one lumen communicating with said at least two distal ends of said perfusion catheter into said coronary vasculature downstream of said occlusion devices.

10. The method of claim 9, further comprising the steps of:
   g) introducing a third distal end of said perfusion catheter through an aortic valve of said heart of said patient;
   h) venting a left ventricle of said heart by withdrawing fluid through a venting lumen communicating with said third distal end of said catheter.

11. The method of claim 1, wherein step a) comprises introducing the distal ends of at least two perfusion catheters into said peripheral artery of said patient; step b) comprises advancing said distal ends of said at least two perfusion catheters into at least two coronary ostia; step c) comprises occluding each of said at least two coronary ostia with an occlusion device proximate each of said distal ends of said at least two perfusion catheters, respectively; and step d) comprises infusing a cardioplegic agent through at least two lumina communicating with said distal ends of said at least two perfusion catheters, respectively, into said coronary vasculature downstream of said at least two occlusion devices.

12. The method of claim 11, further comprising the steps of:

g) introducing a distal end of a venting catheter through an aortic valve of said heart of said patient;

h) venting a left ventricle of said heart by withdrawing fluid through a venting lumen communicating with said distal end of said venting catheter.

13. The method of claim 1, wherein step c) comprises inflating an inflatable occlusion device to occlude said coronary ostium.

14. The method of claim 1, wherein step a) comprises the substeps of:

introducing a guide catheter having at least one internal lumen into said peripheral artery of said patient; and introducing said at least one distal end of said at least one perfusion catheter through said at least one internal lumen of said guide catheter.

15. The method of claim 11, wherein step a) comprises the substeps of:

introducing a guide catheter having at least one internal lumen into said peripheral artery of said patient; and introducing the distal ends of said at least two perfusion catheters through said at least one internal lumen of said guide catheter.

16. The method of claim 11, wherein step a) comprises the substeps of:

introducing a guide catheter having at least two internal lumina into said peripheral artery of said patient; and introducing the distal end of a first perfusion catheter through a first internal lumen in said guide catheter, and introducing the distal end of a second perfusion catheter through a second internal lumen in said guide catheter.

17. The method of claim 1 further comprising the step of:

i) performing coronary artery bypass graft surgery on the arrested heart of the patient.

18. The method of claim 1, further comprising the step of:

infusing oxygenated blood into the patient through an arterial cannula; and the inserting step is carried out by passing the at least one perfusion catheter through the arterial cannula;

the advancing step being carried out with the at least one perfusion catheter being slidably moved relative to the arterial cannula.

19. A method of cooling myocardial tissue in a heart of a patient, the heart having a coronary vasculature, comprising the steps of:

a) introducing a distal end of at least one catheter into a peripheral artery of said patient;

b) advancing said distal end of said at least one catheter from said peripheral artery into at least one coronary ostium of a coronary artery communicating with said coronary vasculature of said patient;

c) occluding said coronary ostium of the coronary artery with an occlusion device mounted to the at least one catheter;

d) infusing a cold fluid into said coronary vasculature through a first lumen;

e) withdrawing fluid from said coronary vasculature through a second lumen.

20. The method of claim 1, wherein step d) comprises infusing a cold fluid containing a cardioplegic agent into said coronary vasculature through said first lumen in a greater quantity than the quantity of fluid withdrawn from said coronary vasculature through said second lumen in step e), whereby at least some of said cold fluid containing a cardioplegic agent is forced to flow through said coronary vasculature.

* * * * *